United States Patent [19]

Weppner

[11] 4,352,068
[45] Sep. 28, 1982

[54] METHOD OF MEASURING ACTIVITIES BY MEANS OF SOLID ION CONDUCTORS

[75] Inventor: Werner Weppner, Stuttgart, Fed. Rep. of Germany

[73] Assignee: Max-Planck-Gesellschaft zur Förderung der Wissenschaften e.V., Göttingen, Fed. Rep. of Germany

[21] Appl. No.: 161,597

[22] Filed: Jun. 20, 1980

[30] Foreign Application Priority Data

Jun. 28, 1979 [DE] Fed. Rep. of Germany ....... 2926172

[51] Int. Cl.$^3$ ............................................ G01N 27/42
[52] U.S. Cl. .................................................. 324/452
[58] Field of Search ........................ 324/438, 464, 453

[56] References Cited
PUBLICATIONS

Huggins, R. A., Recent Results on Lithium Ion Conductors, (Cent. Mater. Res, Stanford Univ., Stanford, Ca.) Electrochim Acta, 1977, vol. 22, No. 7, pp. 773-781 (Eng).

Primary Examiner—Michael J. Tokar
Attorney, Agent, or Firm—Toren, McGeady & Stanger

[57] ABSTRACT

A method for measuring the activity of a component of a sample medium using a solid ion conductor having N components wherein N is less than or equal to 3 and having one component which corresponds to the component to be measured is disclosed. The process is carried out by first equilibrating the solid ion conductor with the medium and then with the N-2 adjacent phases of the phase system of the N components of the solid ion conductor. Finally, it is equilibrated with a reference electrode and the voltage between the reference electrode and the medium is measured.

7 Claims, 1 Drawing Figure

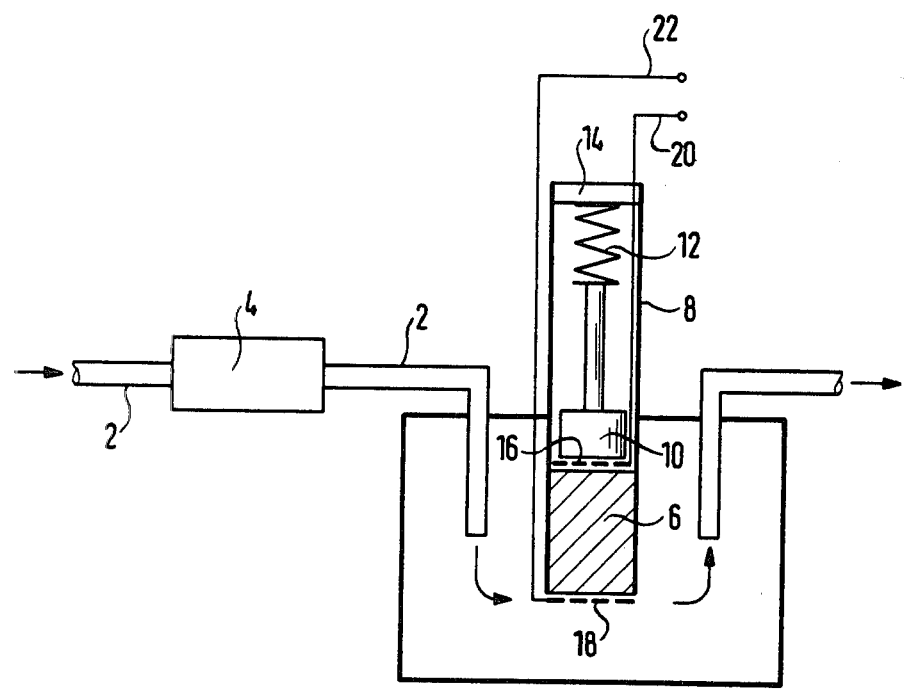

METHOD OF MEASURING ACTIVITIES BY MEANS OF SOLID ION CONDUCTORS

The invention relates to a method of measuring the activity (corresponding to the partial pressure or the concentration at ideal behavior) of a component of a medium by means of a solid ion conductor having N components.

It is the object of the invention to provide a method of this kind which is relatively inexpensive and requires relatively little time and which works directly, quickly, accurately and with satisfactory reproducibility.

For meeting this object, in the case that the ion conductor has at least three components of which one component corresponds to the component to be measured, the method is characterized in that the ion conductor is equilibrated, on the one hand, with the medium having $N-2$ adjacent phases of the phase system of the N components of the ion conductor, and, on the other hand, of a reference electrode which determines the activity of a transferrable ion type in the ion conductor, and that the voltage is measured between this reference electrode and the medium.

For meeting this object, in the case that no component of ion conductor corresponds to the component to be measured, without limiting the number of components of the ion conductor, the method is characterized in that the ion conductor is equilibrated, on the one hand, with the medium having $N-1$ adjacent phases of the phase system of the N-components of the ion conductor and the component to be measured as the $(N+1)$th component, and, on the other hand, with a reference electrode which determines the activity of a transferrable ion type in the ion conductor, and that the voltage is measured between this reference electrode and the medium.

The FIGURE shows an apparatus for carrying out sample medium activity measurement with a solid ion conductor.

Ternary ion conductors are primarily used as ion conductors. In the following, the principle of the invention shall be explained with the aid of these ternary ion conductors. If the ion conductor contains the component to be measured, the ion conductor is equilibrated on the side of the medium to be measured with a second phase which is adjacent in Gibbs' phase triangle. The transferrable ion type in the ion conductor does not have to correspond to the component to be measured.

The voltage of the chain

Reference Electrode | Solid Ternary Ion Conductor | Medium To Be Analyzed Adjacent Phase which is measured relative to the reference electrode for specifying the activity of the transferred ion type, is determined by the activity of the component of the transferrable ion type. In accordance with Gibbs' phase rule, this latter activity results from the equilibrium with the medium and the adjacent phase which, for example, is present as a constituent of the mixture when starting materials in the form of powder are used.

If the ion conductor does not contain the component to be measured, two adjacent phases on the side of the medium to be tested are to be admixed to the ion conductor.

In a preferred embodiment, the method is characterized in that, for measuring the partial pressure of chlorine in the medium, a solid ion conductor of LiAlCl$_4$, an adjacent phase of AlCl$_3$ or of LiCl and a reference electrode determining the activity of lithium in LiAlCl$_4$ are used.

The chlorine may be contained in a gas, a liquid or a solid body.

This results in the following chain

Reference Electrode | LiAlCl$_4$ | Medium to be Measured

AlCl$_3$

LiAlCl$_4$ is a pure ion conductor for lithium ions (W. Weppner and R. A. Huggins, J. Electrochem. Soc. 124, 35 (1977)). The phase border of the LiAlCl$_4$ on the right in the representation is in equilibrium with AlCl$_3$. This can be effected by admixing this compound to the electrolyte, or by electrochemical decomposition, i.e. by removing lithium on the right side of the electrolyte while releasing chlorine gas when a voltage is applied to the chain with the positive pole on the right side. As the reference electrode, a material is to be used which defines the lithium activity on the left side of the solid electrolyte and is in equilibrium with the latter, for example, a mixture of LiCl and Al.

In accordance with Gibbs' phase rule, the pressure of the chlorine of the system to be tested also determines the activities of the aluminum and the lithium at this point. The resulting voltage is based on the difference of the lithium activities between both sides of the solid electrolyte.

The sensor can be used at a low temperature, for example, at room temperature, and up to the melting point at 146° C. The method only requires the determination of voltages. Due to the hydroscopic properties of the LiAlCl$_4$, the system to be tested must be dried in a conventional manner.

Accordingly, the method can be used particularly for the determination of partial pressures of chlorine, to wit, generally in the environmental protection in chlorination plants, or for the monitoring of production, for example, in the manufacture of aluminum.

EXAMPLE

In the galvanic chain

LiCl, Al as

Lithium aluminum chloride (LiAlCl$_4$) is a solid pure ion conductor for lithium ions [W. Weppner and R. A. Huggins, J. Electrochem. Soc. 124, 35 (1977)]. A material is used as the reference electrode which is in equilibrium with LiAlCl$_4$ and which specifies the activity of the lithium in a defined manner, namely a mixture of lithium chloride (LiCl) and aluminum (Al).

Since three phases with three components (LiAlCl$_4$, AlCl and Al) are in equilibrium with one another, according to Gibbs' phase rule, the activities of all components at the phase border are determined between the reference electrode and the electrolyte.

On its free side, the solid electrolyte (LiAlCl$_4$) is in equilibrium with aluminum chloride (AlCl$_3$). This second phase can be formed by a suitable admixing of (LiAlCl$_4$) and (AlCl$_3$) during the preparation from starting materials in the form of powders, or by conducting a current through the chain in such a manner that lithium at the right side of the solid electrolyte (LiAlCl$_4$) is removed and is brought to the reference electrode (LiCl, Al) whereby chlorine (Cl$_2$) is released.

$$\text{LiAlCl}_4 - \text{Li} = \text{AlCl}_3 + 0.5 \text{ Cl}_2 \uparrow \quad (1)$$

The chlorine pressure $P_{Cl_2}$ of the system to be measured determines the activity of the chlorine in aluminum chloride (AlCl$_3$) and in lithium aluminum chloride (LiAlCl$_4$). The aluminum chloride (AlCl$_3$) also determines the activity of the aluminum in both phases. Consequently, the activity of the lithium in the lithium aluminum chloride (LiAlCl$_4$) assumes a defined value which is dependent from the chlorine pressure $P_{Cl_2}$ and which can be measured through the cell voltage E. This is because, in accordance with Gibbs' phase rule, the activities of all components are fixedly adjusted in ternary systems in the case of equilibrium of three phases.

When the chlorine pressure of the medium to be tested is $P_{Cl_2}$ atm, the following cell voltage results $$E' = -1/F [\Delta G_f^\circ(\text{LiAlCl}_4) - \Delta G_f^\circ(\text{AlCl}_3) - (RT/2) \ln pCl_2]; \quad (2)$$

if pure lithium is assumed to be the reference electrode.

$\Delta G_f^\circ$, F, R and T are, respectively, the energy of formation according to Gibbs for standard conditions, the Faraday constant, the general gas constant and the absolute temperature. For $\Delta G_f^\circ$, the following values can be found in the literature:

$$\Delta G_f^\circ(\text{AlCl}_3) = -705.3 + 0.251 \, T[K] \text{ kJ/mole}$$

[I. Barin and O. Knacke, Thermochemical Properties of Inorganic Substances, Springer, Berlin (1973); I. Berin, O. Knacke and O. Kubaschewski, Thermochemical Properties of Inorganic Substances, Supplement, Springer, Berlin (1977)], and $$\Delta G_f^\circ(\text{LiAlCl}_4) = -1169 + 0.395 \, T[K] \text{ kJ/mole}$$

Since the reference electrode is composed of a mixture of LiCl and Al, that voltage must be deducted from the voltage stated in equation (2) which results when the mixture of LiCl and Al is measured relative to pure lithium:

$$E = -1/F [4/3 \Delta G_f^\circ(\text{LiAlCl}_4) - 4/3 \Delta G_f^\circ(\text{LiCl}) - \Delta G_f^\circ(\text{AlCl}_3) - (RT/2 \ln pCl_2] \quad (3)$$

According to the literature [I. Barin and O. Knacke, l.c.], the following holds for Gibbs' energy of formation $\Delta G_f^\circ$ (LiCl)

$$\Delta G_f^\circ \text{ (LiCl)} = -408.2 + 0.803 \, T[K] \text{ kJ/mole}$$

For the initially mentioned chain, this results in the following relationship between the partial chlorine pressure $pCl_2$ of the system tested and the cell voltage E $$\log p_{Cl_2} \text{[atm]} = \frac{0.8686}{RT} \left[ \frac{4}{3} \Delta G_f^\circ(\text{LiAlCl}_4) - \frac{4}{3} \Delta G_f^\circ(\text{LiCl}) - \Delta G_f^\circ(\text{AlCl}_3) + EF \right] \quad (4)$$

and numerically $$\log p_{Cl_2} \text{[atm]} = -\frac{1.008 \times 10^4 (3.20 - E[V])}{T[K]} + 17.59 \quad (5)$$

Maximum and minimum chlorine pressures in applications:

The partial chlorine pressure $P_{Cl_2}$ to be measured may not impair the existence of the two phases LiAlCl$_4$ and AlCl$_3$. However, a minimum pressure of the chlorine is required, so that the chlorine can be equilibrated with the two materials LiAlCl$_4$ and AlCl$_3$. In the case of equilibrium of both phases with Al, this minimum pressure under which LiAlCl$_4$ and AlCl$_3$ are existent is given by $$\log p_{Cl_2}^{min} \text{[atm]} = \frac{0.2895 \, F}{RT} \Delta G_f^\circ(\text{AlCl}_3) \quad (6)$$

$$= -\frac{2.455 \times 10^4}{T[K]} + 8.74$$

At 25° C., this value is approximately $10^{-74}$ atm. Such a low value is practically of no significance.

The maximum partial chlorine pressure is at least 1 atm, as can be seen from the phase diagram, because LiAlCl$_4$ as well as AlCl$_3$ are in equilibrium with a partial chlorine pressure of 1 atm.

By means of the arrangement illustrated in the drawing, chlorine gas was conducted through a line 2 and a drier 4 past the lower side of a solid electrolyte 6 of LiAlCl$_4$. The LiAlCl$_4$ was pulled into a glass tube 8 by melting on (>146° C.). After solidification, there was tightness to gas between the two ends of the LiAlCl$_4$. A LiCl, Al-reference electrode 10 in the form of a small tablet of a mixture of LiCl and Al (approximately 70 m/o Al) was pressed against the solid electrolyte 6 by means of a spring 12. To avoid reactions with air, the glass tube 8 was sealed at the upper rim by means of a pizein pin 14. Thin (5 μm) molybdenum nettings were provided as electrodes 16,18 which firmly adered to the LiAlCl$_4$ by heating them close to the melting point of LiAlCl$_3$ was generated on the measuring side 18 by a current flow of lithium ions toward the LiCl, Al side 10. The drier 4 was required because LiAlCl$_4$ is hygroscopic.

The measurements were carried out at room temperature. The reaction time was very short, approximately in the order of magnitude of one second. The voltage which could be taken off at the electrode leads 20,22 was in the order of magnitude of several hundred mV depending on the concentration of the chlorine gas and increased with increasing chlorine concentration.

I claim:

1. A method of measuring the activity of a component of a sample medium by means of a solid ion conductor composed of a phase system having N components, wherein N is $\leq 3$, wherein one component corresponds to the component to be measured, comprising equilibrating the solid ion conductor first with the medium, then with the N−2 adjacent phases of the phase system of the N components of the solid ion conductor, and finally with a reference electrode and measuring the voltage between the reference electrode and the medium.

2. A method of measuring the activity of a component of a sample medium by means of a solid ion conductor composed of a phase system having N components, none of the components being the same as the component to be measured, comprising first equilibrating the solid ion conductor with the medium, second with N−1 adjacent phases of the phase system of the N components of the solid ion conductor, third with the component to be measured, and fourth with a reference electrode, and then measuring the voltage between the reference electrode and the medium.

3. The method of claim 1 wherein the component to be measured is chlorine, the solid ion conductor is composed of $LiAlCl_4$, and an adjacent phase in the ternary system Li-Al-Cl and a reference electrode which determines the lithium activity in $LiAlCl_4$ are used.

4. The method of claim 3 wherein $AlCl_3$ is used as the adjacent phase.

5. The method of claim 3 wherein LiCl is used as the adjacent phase.

6. The method of claim 3 wherein a reference electrode of LiCl Al is used.

7. The method of claim 3 wherein a reference electrode of $AlCl_3Al$ is used.

* * * * *

UNITED STATES PATENT AND TRADEMARK OFFICE
CERTIFICATE OF CORRECTION

PATENT NO. : 4,352,068

DATED : September 28, 1982

INVENTOR(S) : Werner Weppner

It is certified that error appears in the above-identified patent and that said Letters Patent is hereby corrected as shown below:

Abstract, Line 3, change "less than" to --greater than--.

Column 4, Line 66, change " $\leq$ " to -- $\geq$ --.

Signed and Sealed this

Twelfth Day of July 1983

[SEAL]

Attest:

GERALD J. MOSSINGHOFF

Attesting Officer

Commissioner of Patents and Trademarks